(12) United States Patent
Auvray et al.

(10) Patent No.: US 10,853,956 B2
(45) Date of Patent: *Dec. 1, 2020

(54) DEVICE AND METHOD FOR MEDICAL IMAGING OF CORONARY VESSELS

(71) Applicant: KONINKLIJKE PHILIPS N.V., Eindhoven (NL)

(72) Inventors: Vincent Maurice André Auvray, Meudon (FR); Raoul Florent, Ville D'Avray (FR); Pierre Henri Lelong, Saint-Mande (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/164,483

(22) Filed: Oct. 18, 2018

(65) Prior Publication Data

US 2019/0051002 A1   Feb. 14, 2019

Related U.S. Application Data

(63) Continuation of application No. 15/127,972, filed as application No. PCT/EP2015/055387 on Mar. 16, 2015, now Pat. No. 10,275,896.

(30) Foreign Application Priority Data

Mar. 26, 2014   (EP) ..................................... 14305429

(51) Int. Cl.
*G06T 7/38* (2017.01)
*A61B 6/00* (2006.01)

(52) U.S. Cl.
CPC .............. *G06T 7/38* (2017.01); *A61B 6/5235* (2013.01); *A61B 6/5247* (2013.01); *G06T 2207/10072* (2013.01); *G06T 2207/30048* (2013.01)

(58) Field of Classification Search
None
See application file for complete search history.

(56) References Cited

U.S. PATENT DOCUMENTS

| 8,055,044 B2 | 11/2011 | Mielekamp |
| 2009/0093712 A1 | 4/2009 | Busch |
| 2009/0123046 A1 | 5/2009 | Mielekamp |
| 2013/0294667 A1 | 11/2013 | Zheng |

OTHER PUBLICATIONS

Quatember, Bernhard et al "Development of an Accurate Method for Motion Analysis of the Heart Wall Based on Medical Imagery", Jan. 2012, Computer Aided System Theory—Eurocast 2011, pp. 248-255.

(Continued)

*Primary Examiner* — Justin P. Misleh

(57) ABSTRACT

A device for medical imaging of coronary vessels includes a data extracting module configured to extract a first vessel map from computed tomography angiography data covering at least one reference cardiac phase and a set of second vessel maps from three-dimensional rotational angiography data covering at least one cardiac cycle. An interpolation module is configured to generate a series of warped versions of the first vessel map aligned with the set of second vessel maps, the series starting at the at least one reference cardiac phase. A merging module is configured to merge the series and the set of second vessel maps at the different phases in order to generate a final imaging map of the coronary vessels.

6 Claims, 3 Drawing Sheets

(56) References Cited

OTHER PUBLICATIONS

Blondel, Christophe et al "4D Deformation Field of Coronary Arieries from Monoplane Rotational X-ray Angiography", International Congress Series, Excerpta Medica, vol. 1256, Jun. 2003, pp. 1073-1078.

Movassaghi, B. et al "4D Coronary Artery Reconstruction based on Retrospectively Gated Rotational Angiography: First in-human Results", Proceedings of SPIE, vol. 6509, Mar. 2007.

Rinck, Daniel et al "Shape-Based Segmentation and Visualization Techniques for Evaluation of Atherosclerotic plaques in Coronary Artery Disease", Proceedings of SPIE, vol. 6141, Mar. 2006.

Haberl, R. et al "Multislice Spiral Computed Tomographic Angiography of Coronary Arteries in Patients with Suspected Coronary Artery Disease: An Effecitve Filter before Catheter Angiography", American Heart Journal, vol. 149, No. 6, Jun. 2005.

Quatember, Bernhard et al "Geometric Modeling and Motion Analysis of the Epicardial Surface of the Heart", Science Direct Mathematics and Computers in Simulation, vol. 81, No. 3, Nov. 2010, pp. 608-622.

Wink, Onno et al "Coronary Computed Tomographic Angiography in the Cath Lab: Current Applications and Future Developments", Cardiology Clinics, Advances in Coronary Angiography, vol. 27, No. 3, Aug. 2009, pp. 513-529.

Metz, Coert T. et al Registration of 3D+t Coronary CTA and Monoplane 2D+t X-Ray Angiography, 2013 IEEE.

Jandt, Uwe et al "Automatic generation of 3D coronary artery centerlines using rotational X-ray angiograpy", Medical Image Analysis, vol. 13, No. 6, Dec. 2009—Abstract Only.

Magro, M. et al "Computed tomography as a tool for percutaneous coronary intervention of chronic total occlusions", EuroIntervention,May 2010—Abstract Only.

Shah, Pinak B. "Management of Coronary Chronic Total Occlusion", Circulation, Clinician Update 2011.

Ruijters, Daniel et al "Vesselness-based 2D-3D Registration of the Coronary Arteries", Int J. Cars, 2009.

DEVICE AND METHOD FOR MEDICAL IMAGING OF CORONARY VESSELS

CROSS-REFERENCE TO PRIOR APPLICATIONS

This application is a Continuation of application Ser. No. 15/127,972, filed Sep. 21, 2016, which is the U.S. National Phase application under 35 U.S.C. § 371 of International Application No. PCT/EP2015/055387, filed on Mar. 16, 2015, which claims the benefit of European Patent Application No. 14305429.4, filed on Mar. 26, 2014. These applications are hereby incorporated by reference herein.

FIELD OF THE INVENTION

The present invention relates to a device and a method for medical imaging of coronary vessels.

BACKGROUND OF THE INVENTION

U.S. Pat. No. 8,055,044 B2 describes a system for visualization of blood vessels and bones. One of two data sets, originating from two different radiological methods is processed to generate interim results, yielded by an operation on one of the data sets. The interim results are used to modify the other data set. Different imaging capabilities of the employed radiological methods promote a particular task, e.g. the segmentation of a given type of tissue.

When the combined data of both methods is displayed, clinical users benefit from the complementary information. It is conducted, that only relevant information is presented to the user, as to avoid irrelevant data obscuring any data of interest. Therefore, the data to be displayed is further filtered based on content, e.g. the type of tissue, and on location. Three-dimensional computer tomography and three-dimensional rotational angiography are particularly applicable radiological methods.

US 2009/0123046 A1 describes a system and a method of generating intraoperative three-dimensional image data including the processes of acquiring baseline three-dimensional image data of a region of interest. Non-contrast three-dimensional image data of the region and intra-operative two-dimensional image data of the region are acquired in addition.

The intra-operative two-dimensional image data and the baseline three-dimensional image data are each aligned to the non-contrast three-dimensional image data, whereby a rendering of intra-operative three-dimensional image data results from the alignment of both the baseline three-dimensional and intra-operative two-dimensional image data to the non-contrast three-dimensional image data.

US 2009/093712 A1 describes a method for navigating a catheter with a catheter tip through a blockage region in a vessel, especially a coronary vessel, whereby the catheter is pushed forward under real-time radiological observation. For this purpose, a three-dimensional path through the blockage region is determined by reference to a set of sectional images or a three-dimensional representation of the blockage region, recorded beforehand as part of a preliminary investigation, whereby a data set including the path coordinates is brought into register with the real-time radiological images, and whereby the path or a projection of the path is visualized on a display, overlaid on the real-time radiological images.

An article by Quatember, Bernhard, et al., "Development of an Accurate Method for Motion Analyses of the Heart Wall Based on Medical Imagery", Computer Aided Systems Theory—EUROCAST 2011, Springer Berlin Heidelberg, pp. 248-255, (hereinafter "document D1" or "D1") describes a technique for tracking and analyzing the regional motion of the epicardial surface of the heart throughout the cardiac cycle, based on cardiac CT and biplane cineangiography. The epicardial surface is segmented from 3D CT data. Selected bifurcation points of the epicardial arteries are defined as landmarks. Based on these landmarks, the epicardial surface is registered to a 3D reconstruction of the coronary artery tree made from the biplane cineangiograms. The initial registration is used as a basis for a time series of transformations of the epicardial surface throughout the cardiac cycle.

The recanalization of chronically total occluded, CTO, coronary arteries is one of the most difficult percutaneous interventions, because the course of the occluded part of the vessel is invisible in angiography. The occluded portion being visible in computed tomography angiography, CTA, exams, it has been proposed to extract a complete map of the coronary arteries from the computed tomography, CT, and to present it aligned with the angiography to help planning and navigation in the cath lab.

However, cardiac CTA are only performed at diastole in practice. As a result, the complete coronary map is only available at one heart phase. This is an important limitation for some applications like three-dimensional cardiac roadmapping in the case of CTO.

SUMMARY OF THE INVENTION

There may be a need to improve the digital image processing for medical imaging of coronary vessels and coronary mapping.

These needs are met by the subject-matter of the independent claims. Further exemplary embodiments are evident from the dependent claims and the following description.

An aspect of the invention relates to a device for medical imaging of coronary vessels, the device comprising: a data extracting module configured to extract a first vessel map from computed tomography angiography data covering at least one reference cardiac phase and a set of second vessel maps from three-dimensional rotational angiography data covering at least one cardiac cycle; an interpolation module configured to generate a series of warped versions of the first vessel map aligned with the set of second vessel maps, the series starting at the at least one reference cardiac phase; and a merging module configured to merge the series and the set of second vessel maps at the different phases in order to generate a final imaging map of the coronary vessels.

A further aspect of the invention relates to an X-ray medical imaging system comprising a computed tomography angiography device providing computed tomography angiography data, a three-dimensional rotational angiography device providing three-dimensional rotational angiography data and a device for medical imaging of coronary vessels.

A further aspect of the invention relates to a method for medical imaging of coronary vessels, the method comprising the steps of: extracting a first vessel map from computed tomography angiography data covering at least one cardiac phase and a set of second vessel maps from three-dimensional rotational angiography data covering at least one cardiac cycle; generating a series of versions the first vessel map based on estimated motions of the coronary vessels and the initial alignment of both datasets at the at least one reference phase; interpolating the set of second vessel maps from the reference cardiac phase to any other phase based on the estimated motions of the coronary vessels; and merging the series and the set of second vessel maps at different phases in order to generate a final imaging map of the coronary vessels.

The present invention provides an approach to rely on a C-arm CT reconstruction of three-dimensional rotational angiography of the coronary arteries to generate a complete multiphase map. Indeed, accurate three-dimensional maps of the injected coronaries (over which the occluded segments are invisible) can be extracted from the three-dimensional rotational angiography, 3DRA, at any given heart phase.

The present invention provides to warp the CTA coronary map over each of the 3DRA coronary maps, in order to generate accurate multiphase coronary maps that show the occluded vessel segments. In other words, a final imaging map of the coronary vessels is generated, in which vessel segments that are occluded in the 3DRA vessel maps have been made visible based on their appearance in the CT vessel map.

The present invention advantageously provides to rely on a set of second coronary vessel maps, which presents the opposite characteristics: they can be extracted accurately at any given heart phase, but they show only the vessel parts that are injected—and thus miss the occluded parts. These second coronary maps can be gained from a 3DRA, typically an X-per swing acquisition or any other single or dual axis rotational coronary angiography.

The present invention advantageously provides to create coronary vessel maps that combine the advantage of the CTA-based and the 3DRA-based maps. In a first step, both maps are registered at diastole, when the arteries geometry is similar. In a second step, the motion from the arteries is estimated from the 3DRA maps, and applied to the CTA-maps in order to create the missing phases of the CTA-maps. Finally, both maps are merged.

The present invention advantageously protects the alignment of the CTA-based coronary map with the 3DRA-based coronary map; the coronary vessel maps could be aligned directly, without going through the two phase's motion compensation.

The present invention can be advantageously applied for treatments of coronary chronic total occlusions, in short CTO treatments, in PCI, percutaneous coronary intervention. The multiphase coronary maps can for instance be displayed in real time next to the fluoroscopic image. Alternatively, they can be properly positioned and overlaid over the fluoroscopic image (three-dimensional road-mapping).

The present invention may be advantageously applied to C-arm based systems any other single or dual axis rotational coronary angiography system.

According to an exemplary embodiment of the invention, the data extracting module is configured to extract the first vessel map from the computed tomography angiography data covering a diastole of the cardiac cycle as the at least one reference cardiac phase.

According to an exemplary embodiment of the invention, the interpolation module is configured to, at reference cardiac phase, register from the first vessel map to the set of second vessel maps maps and to interpolate from the reference cardiac phase to any other phase based on motions of the coronary vessels estimated of the set of second vessel maps. This advantageously provides to create coronary maps that combine the advantage of the CTA-based and the 3DRA-based maps.

According to an exemplary embodiment of the invention, the interpolation module is configured to align the first map and the set of second maps by aligning common branches of the coronary vessels. This is advantageously applied for treatments of coronary chronic total occlusions.

According to an exemplary embodiment of the invention, the merging module is configured to merge the warped series and the set of second maps by applying successively estimated motions over the first vessel map. This advantageously generates accurate multiphase coronary maps that show the occluded vessel segments.

According to an exemplary embodiment of the invention, the merging module is configured to add calcified or otherwise occluded part of the vessels, visible in the first vessel map (e.g. a CT vessel map), to moving vessels detected on the set of second vessel maps (e.g. a set of 3DRA vessel maps covering an entire cardiac cycle)

According to an exemplary embodiment of the invention, the at least one cardiac phase is a diastole of the cardiac cycle.

According to an exemplary embodiment of the invention, at the reference cardiac phase, the step of registering from the first map to the set of second maps is conducted. This advantageously provides to create coronary maps that combine the advantage of the CTA-based and the 3DRA-based maps.

According to an exemplary embodiment of the invention, the step of merging of the series and the set of second maps is conducted by aligning common branches of the coronary vessels.

According to an exemplary embodiment of the invention, the step of merging the series and the set of second maps is conducted by applying successively estimated motions. This advantageously generates accurate multiphase coronary maps that show the occluded vessel segments.

According to an exemplary embodiment of the invention, the step of merging adds calcified part of the vessels, visible in the first vessel map, to the moving vessels detected on the set of second maps.

According to an exemplary embodiment of the invention, the method further comprises the step of visualizing the final imaging map of the coronary vessels. This advantageously provides visualization of vessel segments occluded in the set of second maps.

The invention further relates to medical imaging of coronary vessels as used for molecular diagnostics, molecular pathology, in particular for cardiac applications, biological sample analysis, chemical sample analysis, food analysis, and/or forensic analysis. Molecular diagnostics may for example be accomplished with the help of magnetic beads or fluorescent particles that are directly or indirectly attached to target molecules.

The computer program may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit within an application specific integrated circuit, ASIC.

The invention can be implemented in digital electronic circuitry, or in computer hardware, firmware, software, or in combinations thereof, e.g. in available hardware of conventional mobile devices or in new hardware dedicated for processing the methods described herein.

A more complete appreciation of the invention and the attendant advantages thereof will be more clearly understood by reference to the following schematic drawings, which are not to scale, wherein.

DETAILED DESCRIPTION OF EMBODIMENTS

Figure 1:
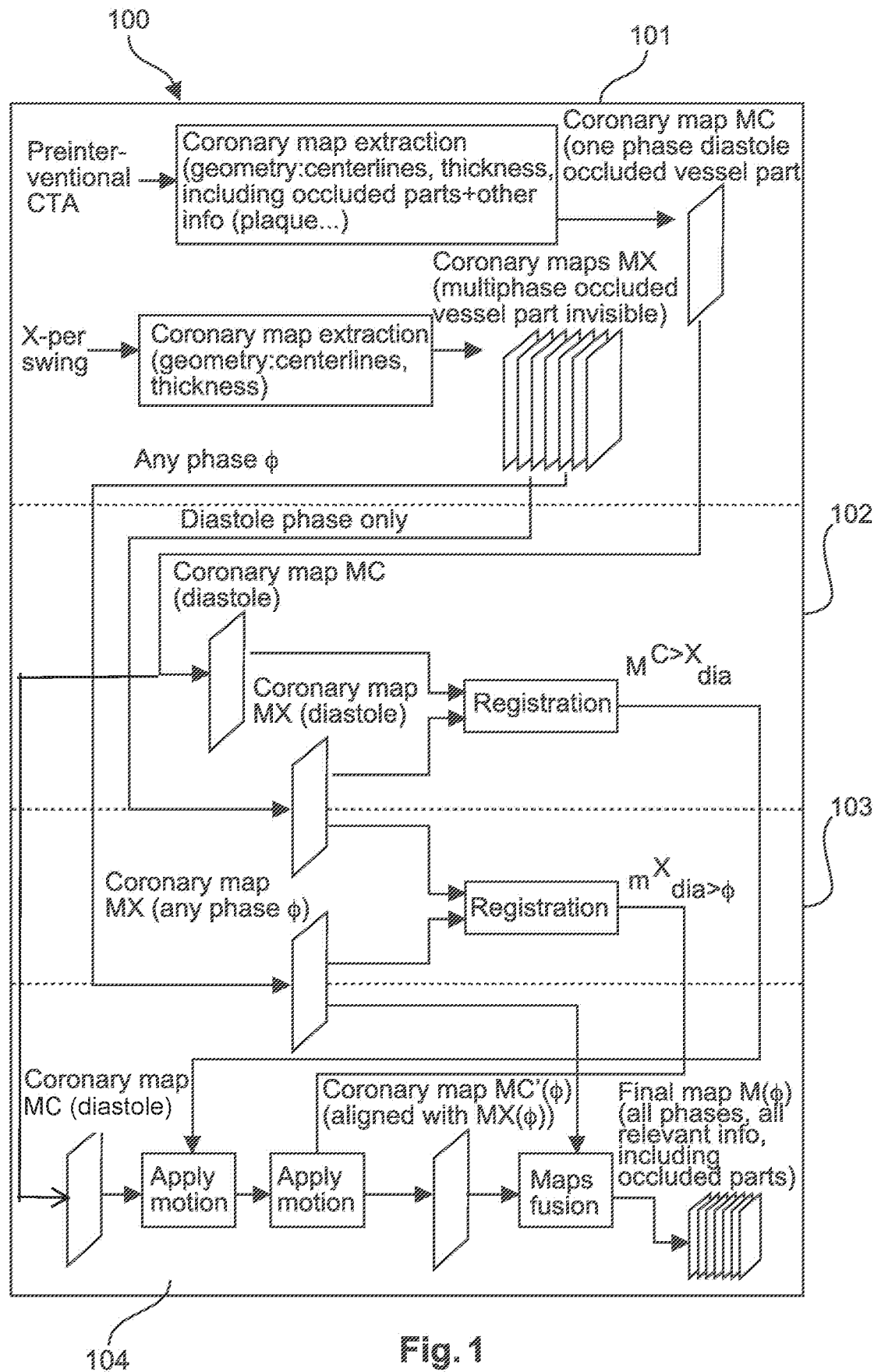
FIG. 1 shows a schematic flowchart diagram of a method for medical imaging of coronary vessels according to an exemplary embodiment of the invention.

The illustration in the drawings is schematically and not to scale. In different drawings, similar or identical elements are provided with the same reference numerals. Generally, identical parts, units, entities or steps are provided with the same reference symbols in the figures.

FIG. 1 shows a schematic flowchart diagram of a method for medical imaging of coronary vessels according to an exemplary embodiment of the invention.

The method is visualized in terms of a function block diagram. A function block contains input variables, output variables, through variables, internal variables, and an internal behavior description of the function block. Function blocks are used primarily to specify the properties of a user function. Many software languages are based on function blocks.

Figure 2:
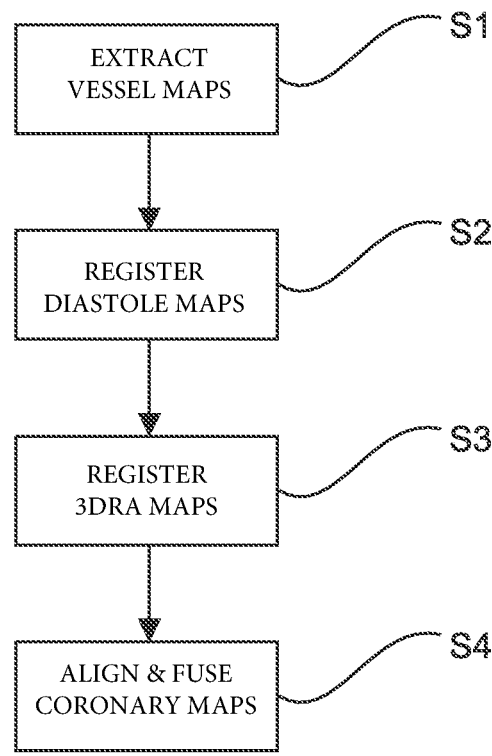
FIG. 2 shows a schematic flowchart diagram of a method for medical imaging of coronary vessels according to an exemplary embodiment of the invention.

The method or function block 100 may comprise, as sub-elements, four steps S1, S2, S3, S4 or four function blocks 101, 102, 103, 104:

In a first function block 101, corresponding to the first step S1 as shown in FIG. 2, a coronary maps extraction is conducted, wherein the coronary maps extraction may be conducted in both in CTA and 3DRA data.

The output of this first step may be the following:
a first vessel map from computed tomography angiography data, called map MC, corresponding to one heart phase (diastole) or any other reference point with any phase, and on which the missing vessel parts are visible.
a series of second maps $MX(\phi)$ from the 3DRA, corresponding to different phases $\phi$ (as asked by the user, or required by the application). They present a superior spatial resolution, but the non-injected vessel parts (mainly, the occluded coronary segments) are invisible on it.

In a second function block 102, corresponding to the second step S2 as shown in FIG. 2, a coronary maps registration at diastole may be conducted.

Aligning the common branches of the maps MC and MX(diastole) may be conducted. Most of the branches are visible on both maps (the only exceptions being of the occluded segments).

Several algorithms exist to perform that step differing in particular in the type of motions they are considering, from rigid to very local. These algorithms preferably are initialized by an approximate knowledge on the pose of the patient under examination when both volumes (CTA and 3DRA) were acquired.

In a third function block 103, corresponding to the third step S3 as shown in FIG. 2, a registration of the 3DRA coronary maps at different phases is conducted.

Herewith, registering the branches from the maps MX(diastole) and $MX(\phi)$ is performed.

It may also be possible to register maps of successive phases, then to propagate the estimated motions (from diastole to diastole+1, . . . , $\phi$-2 to $\phi$-1 and $\phi$-1 to $\phi$), and potentially to refine that motion, than to directly register from the diastole to $\phi$.

According to a further exemplary embodiment of the present invention, the same algorithms used in the previous step or function block can also be used here, though the constraint on robustness can be relaxed (no extra branch, for instance, calcified, are expected from one map to the next).

In a fourth function block 104, corresponding to the fourth step S4 as shown in FIG. 2, coronary maps alignment and fusion may be performed.

By applying successively the estimated motions over MC, we first warp it from the CTA world to the 3DRA map (for instance at diastole), and then from the diastole to the considered phase. The resulting map $MC'(\phi)$ is perfectly aligned with $MX(\phi)$. Finally, merging both maps is performed by preserving the information of interest that are present in both types of coronary maps.

A further implementation would display $MC'(\phi)$. In that case, generating a 3D+t multiphase coronary map from the CT aligned with the cath lab is performed. A catheterization laboratory or cath lab is an examination room in a hospital or clinic with diagnostic imaging equipment used to visualize the arteries of the heart. The generating of the 3D+t multiphase could be used as a live multiphase roadmap for the CTO treatment, for instance.

According to an exemplary embodiment of the invention, the coronary maps gained from the X-per swing present a superior spatial resolution. Analyzing the maps MC' for the occluded segments may be performed, wherein those that are not present in MX are processed, extracted and added to the maps MX. The augmented 3D+t multiphase MX maps may be further added.

According to an exemplary embodiment of the invention, the finally merged maps do not need to be restricted to pure geometrical aspects. Information about the nature of the plaque (gained from the CTA) can also be used there.

FIG. 2 shows a schematic flowchart diagram of a method for medical imaging of coronary vessels according to an exemplary embodiment of the invention.

The method for medical imaging of coronary vessels may comprise the following steps.

As a first step of the method, extracting S1 a first vessel map from computed tomography angiography data covering at least one cardiac phase and a set of second vessel maps from three-dimensional rotational angiography data covering at least one cardiac cycle is conducted.

As a second step of the method, generating S2 a series of warped versions of the first vessel map based on the alignment of the coronary vessels is performed.

As a third step of the method, interpolating S3 the set of second maps from the reference cardiac phase to any other phase based on the estimated motions of the coronary vessels is performed.

As a fourth step of the method, merging S4 the series and the set of second maps at different phases in order to generate a final imaging map of the coronary vessels is conducted.

According to an exemplary embodiment of the invention, these steps may be mixed or simultaneously processed.

Figure 3:
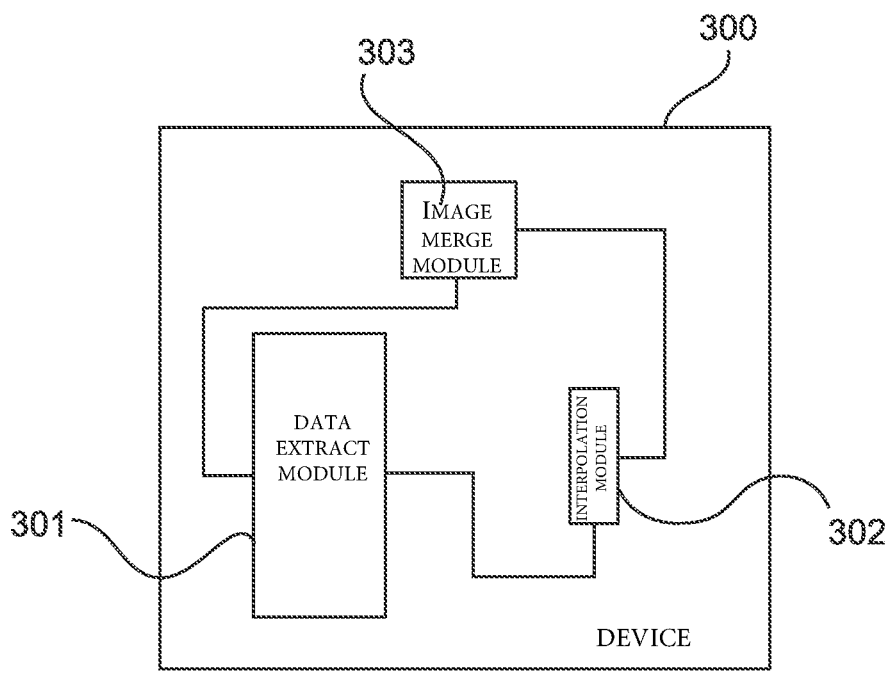
FIG. 3 shows a schematic diagram of a device for medical imaging of coronary vessels according to an exemplary embodiment of the invention.

FIG. 3 shows a schematic diagram of a device for medical imaging of coronary vessels according to an exemplary embodiment of the invention.

A device 300 for medical imaging of coronary vessels may comprise a data extracting module 301 configured to extract a first vessel map from computed tomography angiography data covering at least one reference cardiac phase and a set of second vessel maps from three-dimensional rotational angiography data covering at least one cardiac cycle.

The device may further comprise an interpolation module 302 configured to generate a series of warped versions of the first map aligned with the set of second maps, the series starting at the at least one reference cardiac phase.

Further, the device may comprise a merging module 303 configured to merge the series and the set of second maps at the different phases in order to generate a final imaging map of the coronary vessels.

Figure 4:
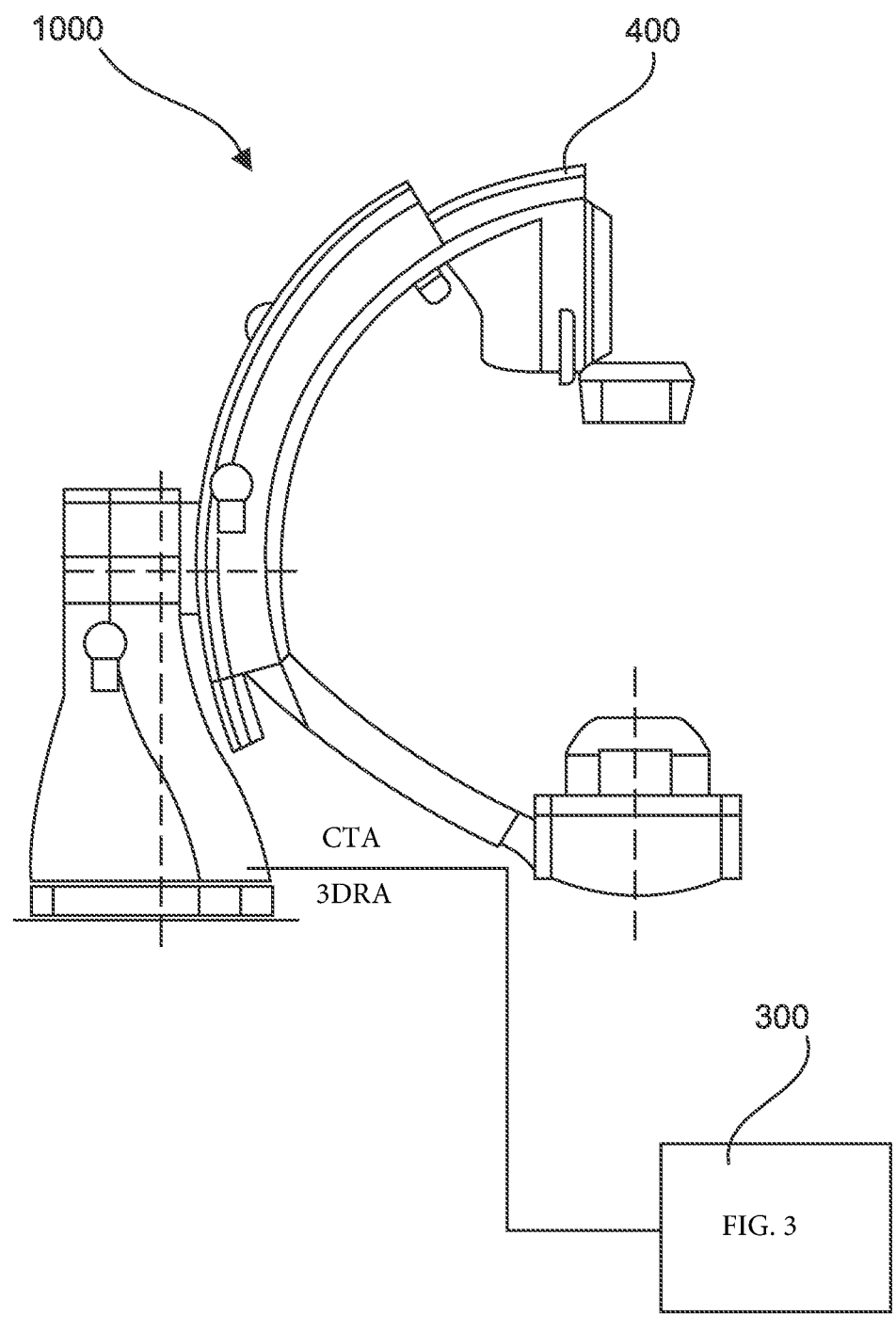
FIG. 4 shows a schematic diagram of an X-ray medical imaging system for medical imaging of coronary vessels according to an exemplary embodiment of the invention.

FIG. 4 shows a schematic diagram of an X-ray medical imaging system for medical imaging of coronary vessels according to an exemplary embodiment of the invention.

An X-ray medical imaging system 1000 may comprise a computed tomography angiography device 400 providing computed tomography angiography data, a three-dimensional rotational angiography device 400 providing three-dimensional rotational angiography data and a device 300 for medical imaging of coronary vessels. Contrary to the embodiment as depicted in FIG. 4, the computed tomography angiography device 400 and the three-dimensional rotational angiography device 400 may be constructed as separated and single units.

In another exemplary embodiment of the present invention, a computer program or a computer program element is provided that is characterized by being adapted to execute the method steps of the method according to one of the preceding embodiments, on an appropriate system.

According to a further exemplary embodiment of the present invention, the computer program element might therefore be stored on a computer unit, which might also be part of an embodiment of the present invention. This computing unit may be adapted to perform or induce a performing of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network.

According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims.

However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for medical imaging of coronary vessels, the method comprising the steps of:

extracting a first 3D vessel map of coronary vessels from computed tomography angiography (CTA) data, said CTA data resulting from a CTA performed during a reference cardiac phase, and extracting a set of second 3D vessel maps of the coronary vessels from three-dimensional rotational angiography (3DRA) data, said 3DRA data resulting from a 3DRA performed during at least one cardiac cycle having phases inclusive of said reference cardiac phase;

registering one second 3D vessel map of the set of second 3D vessel maps, said one second 3D vessel map having been extracted from the 3DRA data resulting from the 3DRA performed during the reference cardiac phase, with the first 3D vessel map extracted from the CTA data, said registering being based on an alignment of the coronary vessels in the first 3D vessel map extracted from the CTA data and the coronary vessels in said one second 3D vessel map of the set of second 3D vessel maps, said registering forming first estimated motions;

registering said one second 3D vessel map extracted from the 3DRA data resulting from the 3DRA performed during the reference cardiac phase to other second 3D vessel maps of the set of second 3D vessel maps, said other second 3D vessel maps extracted from the 3DRA data resulting from the 3DRA performed during other cardiac phases successive to the reference cardiac phase in the at least one cardiac cycle to form second estimated motions;

warping the first 3D vessel map to said one second 3D vessel map, by applying said first estimated motions to the first 3D vessel map, to form a first warped 3D vessel map;

warping the first warped 3D vessel map to the other second 3D vessel maps, by applying said second estimated motions to the first warped 3D vessel map, to form a set of second warped 3D vessel maps; and simultaneously displaying the set of second warped 3D vessel maps and the set of second 3D vessel maps.

2. The method for medical imaging of coronary vessels according to claim 1, wherein the reference cardiac phase is a diastole phase of a cardiac cycle.

3. The method for medical imaging of coronary vessels according to claim 1, wherein the set of second 3D vessel maps are contrast enhanced images in which calcium deposits are not visible, and wherein the warping steps add calcium deposits visible in the first 3D vessel map to the set of second 3D vessel maps.

4. The method for medical imaging of coronary vessels according to claim 1, wherein the step of displaying adds calcified part of the vessels, visible in the first 3D vessel map, to moving vessels of the set of second 3D vessel maps.

5. A non-transitory computer-readable medium storing a computer program which, when run on one or more computer processors, causes the one or more computer processors to perform the method according to claim 1.

6. An image processor programmed to perform the method according to claim 1.

* * * * *